United States Patent
Kunikata et al.

(10) Patent No.: US 12,320,773 B2
(45) Date of Patent: Jun. 3, 2025

(54) ELECTROCHEMICAL DETECTION METHOD FOR CATALYTIC REACTION PRODUCT, AND TRANSDUCER

(71) Applicants: JAPAN AVIATION ELECTRONICS INDUSTRY, LIMITED, Tokyo (JP); TOHOKU UNIVERSITY, Miyagi (JP)

(72) Inventors: Ryota Kunikata, Tokyo (JP); Atsushi Suda, Tokyo (JP); Hiroyuki Hayashi, Tokyo (JP); Kosuke Ino, Miyagi (JP); Tomokazu Matsue, Miyagi (JP)

(73) Assignees: JAPAN AVIATION ELECTRONICS INDUSTRY, LIMITED, Tokyo (JP); TOHOKU UNIVERSITY, Miyagi (JP)

( * ) Notice: Subject to any disclaimer, the term of this patent is extended or adjusted under 35 U.S.C. 154(b) by 740 days.

(21) Appl. No.: 17/609,073

(22) PCT Filed: Apr. 10, 2020

(86) PCT No.: PCT/JP2020/016079
§ 371 (c)(1),
(2) Date: Nov. 5, 2021

(87) PCT Pub. No.: WO2020/235247
PCT Pub. Date: Nov. 26, 2020

(65) Prior Publication Data
US 2022/0229010 A1   Jul. 21, 2022

(30) Foreign Application Priority Data
May 20, 2019 (JP) ................. 2019-094379

(51) Int. Cl.
*G01N 27/403* (2006.01)
*G01N 27/416* (2006.01)
*G01N 33/543* (2006.01)

(52) U.S. Cl.
CPC ......... *G01N 27/403* (2013.01); *G01N 27/416* (2013.01); *G01N 33/54306* (2013.01); *G01N 33/5438* (2013.01)

(58) Field of Classification Search
CPC .. C12Q 1/001; G01N 27/3275; G01N 27/403; G01N 27/416; G01N 33/54306; G01N 33/5438
See application file for complete search history.

(56) References Cited

U.S. PATENT DOCUMENTS 6,682,649 B1    1/2004  Petersen et al.
8,470,144 B2 *  6/2013  Suda ................. G01N 27/3272
                                              204/287

(Continued)

FOREIGN PATENT DOCUMENTS

CN   108291891 A    7/2018
EP   3 605 110 A1   2/2020

(Continued)

OTHER PUBLICATIONS

Partial Search Report issued in EP20809596.8, May 17, 2022, English translation.

(Continued)

*Primary Examiner* — Gurpreet Kaur
(74) *Attorney, Agent, or Firm* — Greenblum & Bernstein, P.L.C.

(57) ABSTRACT

Provided is a method for electrochemically detecting a catalytic reaction product that is generated by progress of a catalytic reaction in a first lump of liquid and dissolved in the first lump of liquid, the method including: containing the first lump of liquid and a second lump of liquid in a liquid bath, the second lump of liquid being in contact with the first lump of liquid to form a liquid-liquid interface and not dissolving the catalytic reaction product; arranging a working electrode in the first lump of liquid, and arranging a (Continued)

counter electrode and a reference electrode in the second lump of liquid; and detecting a current flowing through the working electrode by an oxidation or reduction reaction of the catalytic reaction product at the working electrode.

16 Claims, 8 Drawing Sheets

(56) References Cited

U.S. PATENT DOCUMENTS

| | | | |
|---|---|---|---|
| 8,691,061 B2* | 4/2014 | Suda | G01N 27/307 204/287 |
| 2003/0077642 A1 | 4/2003 | Fritsch et al. | |
| 2003/0194709 A1 | 10/2003 | Yang | |
| 2005/0064482 A1 | 3/2005 | Mino | |
| 2009/0000957 A1* | 1/2009 | Dubin | C12Q 1/001 205/688 |
| 2013/0345088 A1 | 12/2013 | Noji et al. | |
| 2017/0176430 A1 | 6/2017 | Noji et al. | |
| 2017/0307564 A1* | 10/2017 | Shen | G01N 21/75 |
| 2019/0086356 A1 | 3/2019 | Hayashi et al. | |
| 2019/0256816 A1 | 8/2019 | Kunikata et al. | |
| 2019/0277828 A1 | 9/2019 | Hiramoto et al. | |
| 2020/0040468 A1 | 2/2020 | Ino et al. | |
| 2020/0173978 A1 | 6/2020 | Hayashi et al. | |
| 2020/0407769 A1 | 12/2020 | Tabata et al. | |

FOREIGN PATENT DOCUMENTS

| | | |
|---|---|---|
| JP | 2005-227096 A | 8/2005 |
| JP | 2006-266795 A | 10/2006 |
| JP | 2010158201 A | 7/2010 |
| JP | 2013-92437 A | 5/2013 |
| JP | 2015-59929 A | 3/2015 |
| JP | 2017-96721 A | 6/2017 |
| TW | 201738557 A | 11/2017 |
| TW | 201814281 A | 4/2018 |
| TW | 201835385 A | 10/2018 |
| WO | 2012/121310 A1 | 9/2012 |
| WO | 2015/040930 A1 | 3/2015 |
| WO | 2016/006208 A1 | 1/2016 |
| WO | WO2018/043733 A1 | 3/2018 |
| WO | 2018/105454 A1 | 6/2018 |
| WO | 2018/181488 A1 | 10/2018 |
| WO | 2019/168200 A1 | 9/2019 |

OTHER PUBLICATIONS

Extended European Search Report in European Counterpart Patent Appl. No. 23162429.7, dated Aug. 21, 2023.
U.S. Appl. No. 17/613,361 to Kunikata et al., filed Nov. 22, 2021.
S. Sakakihara et al., "A Single-Molecule Enzymatic Assay in a Directly Accessible Femtoliter Droplet Array", Lab on a Chip, Oct. 2010, pp. 3355-3362.
Official Communication issued in International Bureau of WIPO Patent Application No. PCT/JP2020/016079, dated Jun. 30, 2020, along with an English translation thereof.
Office Action issued in Taiwan Counterpart Patent Appl. No. 109112588, dated Sep. 11, 2021, along with an English translation thereof.
Office Action in family member Chinese application No. 202080035960.5 dated Nov. 10, 2023 with machine translation of the Office Action.
Office Action in family member Chinese application No. 202080035960.5 dated Aug. 2, 2024 with machine translation of the Office Action.

* cited by examiner

ELECTROCHEMICAL DETECTION METHOD FOR CATALYTIC REACTION PRODUCT, AND TRANSDUCER

TECHNICAL FIELD

The present invention relates to a technique for electrochemically detecting a product generated by progress of a catalytic reaction in a solution and dissolved in the solution.

BACKGROUND ART

Detection sensitivity of a catalytic reaction product generated by catalytic reaction such as enzyme reaction and dissolved in a solution depends on the concentration of the product in the solution. In order to improve the concentration of the product in the solution, for example, longer catalytic reaction time is preferable or a smaller volume of the solution is preferable.

When the volume of the solution is extremely small, evaporation leads to a decrease in the volume of the solution, making detection impossible. Such a problem arises noticeably in the case of a long catalytic reaction time.

Patent literature 1 and Non-patent literature 1 disclose a configuration that can prevent a solution from evaporating. Patent literature 1 discloses, as a technique related to ELISA (Enzyme-Linked ImmunoSorbent Assay), a configuration in which droplets of a hydrophilic solvent, which is an enzyme reaction field, are placed in a storage part (well) and the storage part is sealed with a hydrophobic solvent.

Regarding an ELISA-related technique, Non-patent literature 1 discloses a configuration in which a pattern of hydrophilic region is formed by forming a hydrophobic region on a hydrophilic surface, and droplets located on the pattern of hydrophilic region (that is, the enzyme reaction field) are covered with oil.

PRIOR ART LITERATURE

Patent Literature

Patent literature 1: International Publication No. WO2012/121310

Non-Patent Literature

Non-patent literature 1: S. Sakakihara et al., "A Single-molecule enzymatic assay in a directly accessible femto-liter droplet array", Lab Chip, 2010, 10, 3355-3362

SUMMARY OF THE INVENTION

Problems to be Solved by the Invention

As described above, evaporation of the solution can be prevented by covering a solution, which is a catalytic reaction field, with a liquid which is different from the solution. Thus, it is possible to achieve detection with high sensitivity.

The techniques disclosed in Patent literature 1 and Non-patent literature 1 are spectroscopic detection techniques using a fluorescent substrate and require a large-scale measuring apparatus. Moreover, the fluorescent substrate is expensive. Therefore, these techniques require a large cost.

An object of the present invention is to provide a technique that can inexpensively and easily detect a catalytic reaction product with high sensitivity.

Means to Solve the Problems

The following technical matters are described simply to facilitate the understanding of the main points of the present invention, not to limit the invention claimed in the claims explicitly or implicitly and not to express the possibility of accepting such a limitation that is imposed by a person other than those who will benefit from the present invention (for example, the applicant and the right holder). The general outline of the present invention described from other perspectives can be understood from, for example, the claims of this application as originally filed at the time of application.

The technique disclosed here is an electrochemical detection technique to which the technique that a first lump of liquid, where a catalytic reaction progresses, is covered with a second lump of liquid is applied.

The technique uses a liquid bath that contains a working electrode, a counter electrode, a first lump of liquid and a second lump of liquid.

The first lump of liquid has conductivity. The working electrode is located in the first lump of liquid.

The second lump of liquid has conductivity. The first lump of liquid and the second lump of liquid form a liquid-liquid interface and the catalytic reaction product is insoluble in the second lump of liquid. The counter electrode is located in the second lump of liquid.

The current is detected which flows through the working electrode by an oxidation reduction reaction between the catalytic reaction product and the working electrode.

Effects of the Invention

According to the present invention, it is possible to detect a catalytic reaction product inexpensively and easily with high sensitivity.

BRIEF DESCRIPTION OF THE DRAWINGS

FIGS. 4(a)-4(c) are diagrams for describing an example of the structure that holds the first lump of liquid.

DETAILED DESCRIPTION OF THE EMBODIMENTS

The present embodiment will be described with reference to the accompanying drawings.

Figure 1:
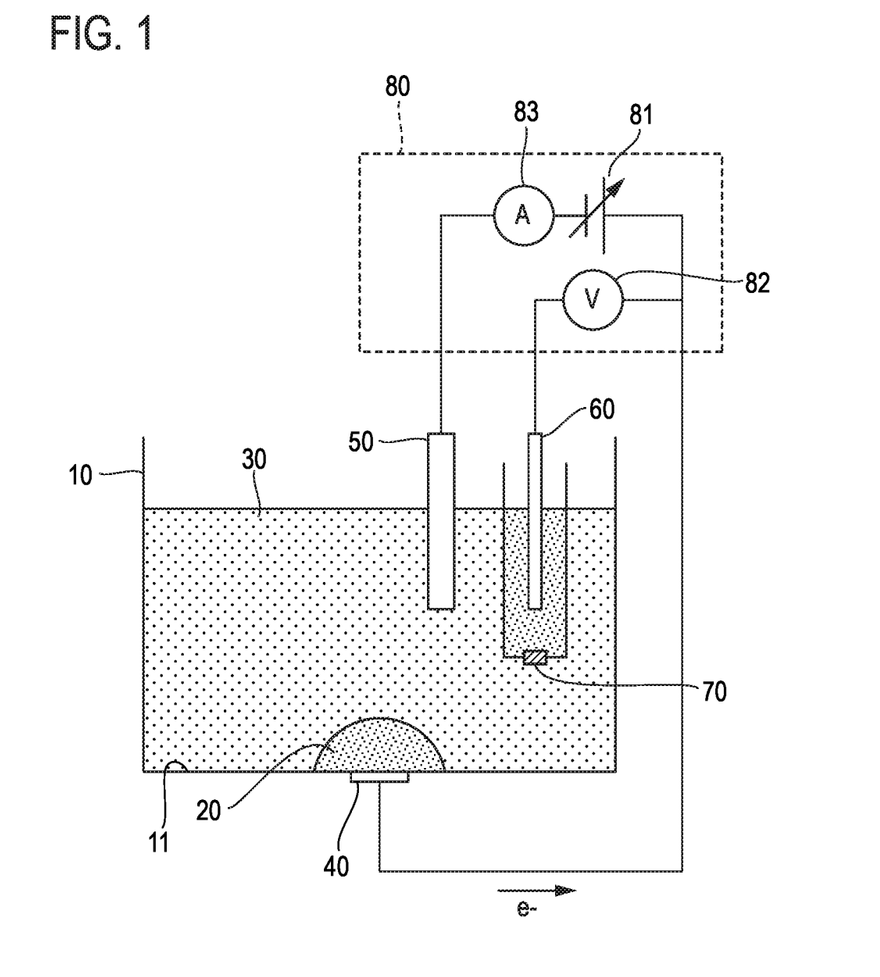
FIG. 1 is a schematic diagram of a detection apparatus.

According to the embodiment, electrochemically detected is a product generated by progress of a catalytic reaction in a first lump of liquid (that is, a lump of solution, which is a catalytic reaction field) and dissolved in the first lump of liquid. FIG. 1 schematically shows a configuration example of a detection apparatus 1 of the present embodiment.

The detection apparatus 1 includes a liquid bath 10, a working electrode 40, a counter electrode 50, a reference electrode 60 and a potentiostat 80. The liquid bath 10 contains a first lump of liquid 20 and a second lump of liquid 30. The first lump of liquid 20 and the second lump of liquid 30 form a liquid-liquid interface (that is, an interface between two liquids). As shown in FIG. 1, the first lump of liquid 20 is placed on a bottom surface 11 of the liquid bath 10 and is covered with the second lump of liquid 30.

The working electrode 40 is located at the bottom surface 11 of the liquid bath 10 and covered with the first lump of liquid 20. That is, the working electrode 40 is in contact with the first lump of liquid 20, whereas it is not in contact with the second lump of liquid 30. The counter electrode 50 and the reference electrode 60 are placed in the second lump of liquid 30 and are electrically connected to the working electrode 40 via the liquid-liquid interface between the first lump of liquid 20 and the second lump of liquid 30. In FIG. 1, reference numeral 70 denotes a salt bridge.

The working electrode 40, the counter electrode 50 and the reference electrode 60 are connected to the potentiostat 80 in this example. The potentiostat 80 functions as a constant-voltage power-supply apparatus and includes a variable power supply 81, a voltmeter 82 and an ammeter 83.

The catalytic reaction product is confined in the first lump of liquid 20 and is not dissolved in the second lump of liquid 30 (that is, the product does not move from the first lump of liquid 20 to the second lump of liquid 30). An oxidation reduction reaction between the catalytic reaction product and the working electrode 40 causes a current to flow through the working electrode 40. By detecting this current, the catalytic reaction product is detected or a quantitative analysis is performed.

Although FIG. 1 shows only one working electrode 40, two or more working electrodes 40 arranged, for example, in an array are generally installed at the bottom surface 11 of the liquid bath 10. When the detection apparatus 1 includes two or more working electrodes 40, the detection apparatus 1 includes two or more first lumps of liquid 20. Each of the two or more working electrodes 40 is covered with the corresponding one of the two or more first lumps of liquid 20. The first lumps of liquid 20 are independent of each other and the first lumps of liquid 20, which are different from each other, are separated by the second lump of liquid 30. The second lump of liquid 30 is a single liquid lump. The second lump of liquid 30 and any one of the two or more first lumps of liquid 20 form a liquid-liquid interface. Each of the two or more first lumps of liquid 20 is covered with the second lump of liquid 30.

Hereinafter, an electrochemical detection method according to the present embodiment applied to ELISA will be described.

According to ELISA, an antigen-antibody complex is detected or quantitative analysis is performed, for example, by labeling an antigen or antibody (that is, immunoglobulin) contained in a sample with an enzyme and detecting a product obtained by a reaction between the enzyme and a substrate. For example, the following operation is performed in a combination of a sandwich ELISA (sandwich ELISA protocol) and an electrochemical detection method. However, operation such as cleaning, incubation (leaving a product at a constant temperature) is not specified.

(1) Binding of capture antibody to a solid phase (the solid phase includes a surface of the working electrode and a surface of a solid substance in the vicinity of the working electrode)
(2) Blocking treatment of the solid phase
(3) Addition of antigen (protein to be detected)
(4) Addition of primary antibody
(5) Addition of enzyme-labeled secondary antibody
(6) Addition of substrate-containing first lump of liquid (by enzyme reaction, enzyme reaction product is accumulated in the vicinity of the working electrode)
(7) Electrochemical detection of enzyme reaction product using the working electrode In the embodiment, an operation of covering the entire first lump of liquid 20 with the second lump of liquid 30 is added as shown in FIG. 1.

The second lump of liquid 30 is insoluble in the conductive first lump of liquid 20, and is a conductive liquid. In ELISA, the first lump of liquid 20 is generally an aqueous solution having a buffering ability, and thus the second lump of liquid 30 is, for example, an organic solvent that is insoluble in water and can dissolve a support electrolyte that is for conductivity.

The organic solvent is preferably a liquid that can be easily handled as a solvent for electrochemical detection, in other words, preferably, the organic solvent is a liquid at ordinary temperature and has low reactivity against water and electrode materials (such as, gold, platinum) within a detection potential range. For example, nitrobenzene, 1,2-dichlorobenzene, 1-nitro-2-(n-octyloxy) benzene, 1,2-dichloroethane, 1,4-dichlorobutane, 1,6-dichlorohexane, 1-octanol or 1,9-decadiene is suitable for the organic solvent.

As the support electrolyte that is soluble in these organic solvents and can impart conductivity to the organic solvents, a support electrolyte used for electrochemical detection in a common non-aqueous solution may be adopted. For example, the support electrolyte is preferably a salt containing, as its anion, any one of chloride ion, bromide ion, iodide ion, sulfate ion, nitrate ion, hyperchloric acid ion, tetrafluoroboric acid ion, hexafluorophosphoric acid ion and sulfonic acid ion, and, as its cation, any one of lithium ion, sodium ion, potassium ion, rubidium ion, cesium ion, ammonium ion and tetraalkyl ammonium ion having alkyl groups of arbitrary chain lengths.

A combination of the labeling enzyme and the substrate is a combination having electrochemical activity and capable of generating a product soluble in the first lump of liquid 20 and not soluble in the second lump of liquid 30. When the first lump of liquid 20 is an aqueous solution and the second lump of liquid 30 is the aforementioned organic solvent, a combination of, for example, alkaline phosphatase and phosphoric acid 4-aminophenyl ester or a combination of, for example, horseradish peroxidase and potassium ferricyanide is suitable for a combination of the labeling enzyme and the substrate.

In the embodiment, as shown in FIG. 1, for high sensitivity detection, an extremely small amount of first lump of liquid 20 is held in contact with the working electrode 40, and further, a state is established in which the working electrode 40, the counter electrode 50 and the reference electrode 60 are electrically connected to one another via the first lump of liquid 20 and the second lump of liquid 30 that covers the first lump of liquid 20. However, when the second lump of liquid 30 is introduced into the liquid bath 10 without taking any special measures after, for example, dropping the first lump of liquid 20 on the working electrode 40 located at the bottom surface 11 of the liquid bath 10, the first lump of liquid 20 is swept away from a top surface of the working electrode 40 due to hydrodynamic action of the second lump of liquid 30. Alternatively, when the density of the first lump of liquid 20 is smaller than the density of the second lump of liquid 30, the first lump of liquid 20 is separated from the working electrode 40 due to buoyancy action. Therefore, the first lump of liquid 20 needs to be held to the top surface of the working electrode 40 strongly enough to exceed the hydrodynamic action and the buoyancy action.

In the embodiment, for instance, the following holding structure is adopted to hold the first lump of liquid 20.

(a) Structure in which the surfaces of all the working electrodes 40 are subjected to a hydrophilic treatment (b) Structure in which annular portions of the bottom surface 11 of the liquid bath 10, each of which surrounding the surface of a corresponding one of the working electrodes 40, are subjected to a hydrophilic treatment (c) Structure in which the surfaces of all the working electrodes 40 and all the annular portions are subjected to a hydrophilic treatment (d) Structure in which all or part of the bottom surface 11 of the liquid bath 10 except the surfaces of all the working electrodes 40 is subjected to a hydrophobic treatment (this structure includes a structure in which a region of the bottom surface 11 of the liquid bath 10 in contact with the second lump of liquid 30 is subjected to a hydrophobic treatment)

(e) Structure in which the surfaces of all the working electrodes 40 are subjected to a hydrophilic treatment and all or part of the bottom surface 11 of the liquid bath 10 except the surfaces of all the working electrodes 40 is subjected to a hydrophobic treatment (f) Structure in which annular portions of the bottom surface 11 of the liquid bath 10, each of which surrounding the surface of a corresponding one of the working electrodes 40, are subjected to a hydrophilic treatment and all or part of the bottom surface 11 of the liquid bath 10 except the surfaces of all the working electrodes 40 and all the annular portions is subjected to a hydrophobic treatment (g) Structure in which the surfaces of all the working electrodes 40 and all the annular portions are subjected to a hydrophilic treatment and all or part of the bottom surface 11 of the liquid bath 10 except the surfaces of all the working electrodes 40 and all the annular portions is subjected to a hydrophobic treatment FIGS. 2A, 2B, 2C, 2D, 2E, 3A, 3B and 3C show examples of the above-described holding structure of the first lump of liquid 20. In the drawings, reference numeral 91 denotes hydrophilic-treated region, reference numeral 92 denotes hydrophobic-treated region. From the standpoint of easy-to-understand illustration, only one working electrode 40 is taken as an example in FIGS. 2A, 2B, 2C, 2D, 2E, 3A, 3B and 3C, and the working electrode 40 located at the bottom surface 11 of the liquid bath 10 has a circular surface shape in this example.

Figure 2A:
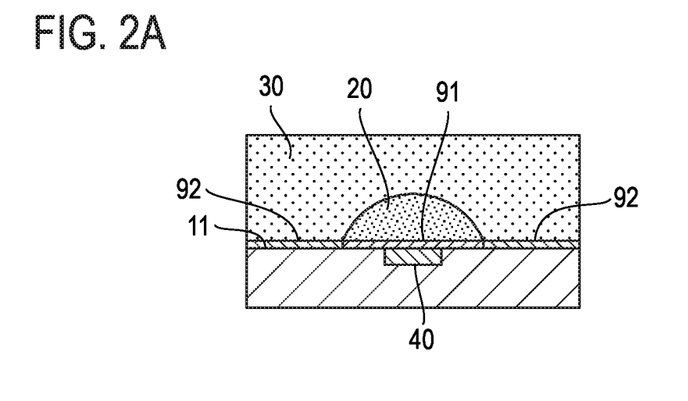
FIG. 2A is a diagram illustrating a first example of a structure that holds a first lump of liquid.

FIG. 2A shows example (g) in which the surface of the working electrode 40 and the annular portion of the bottom surface 11 of the liquid bath 10, which surrounds the surface of the working electrode 40, are subjected to a hydrophilic treatment and the region of the bottom surface 11 of the liquid bath 10 except the surface of the working electrode 40 and the annular portion is subjected to a hydrophobic treatment.

Figure 2B:
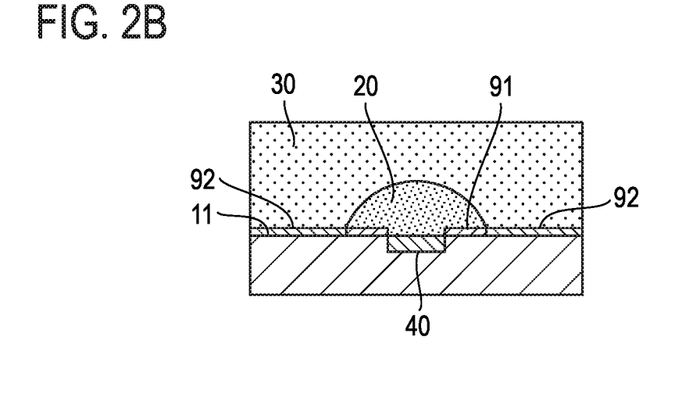
FIG. 2B is a diagram illustrating a second example of the structure that holds the first lump of liquid.

FIG. 2B shows example (f) in which the surface of the working electrode 40 is not subjected to a hydrophilic treatment, but only the annular portion of the bottom surface 11 of the liquid bath 10, which surrounds the surface of the working electrode 40, is subjected to a hydrophilic treatment, and further the region of the bottom surface 11 of the liquid bath 10 except the surface of the working electrode 40 and the annular portion is subjected to a hydrophobic treatment.

Figure 2C:
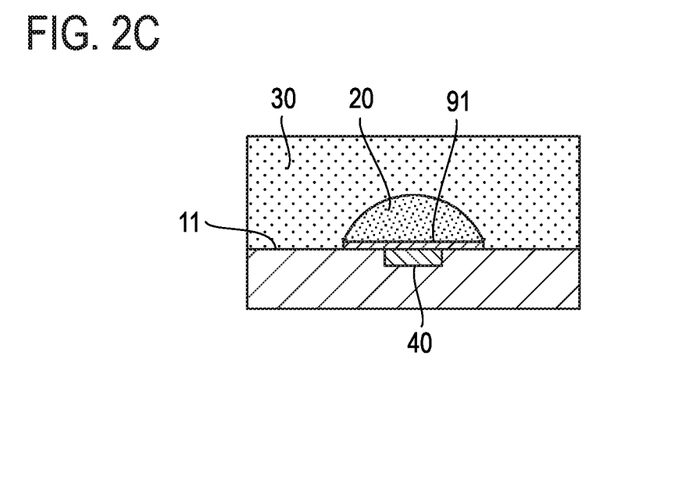
FIG. 2C is a diagram illustrating a third example of the structure that holds the first lump of liquid.

FIG. 2C shows example (c) in which the surface of the working electrode 40 and the annular portion of the bottom surface 11 of the liquid bath 10, which surrounds the surface of the working electrode 40, are subjected to a hydrophilic treatment.

Figure 2D:
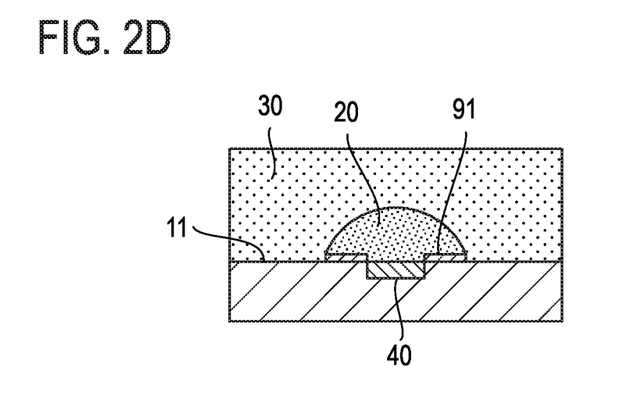
FIG. 2D is a diagram illustrating a fourth example of the structure that holds the first lump of liquid.

FIG. 2D shows example (b) in which the surface of the working electrode 40 is not subjected to a hydrophilic treatment, but only the annular portion of the bottom surface 11 of the liquid bath 10, which surrounds the surface of the working electrode 40, is subjected to a hydrophilic treatment.

Figure 2E:
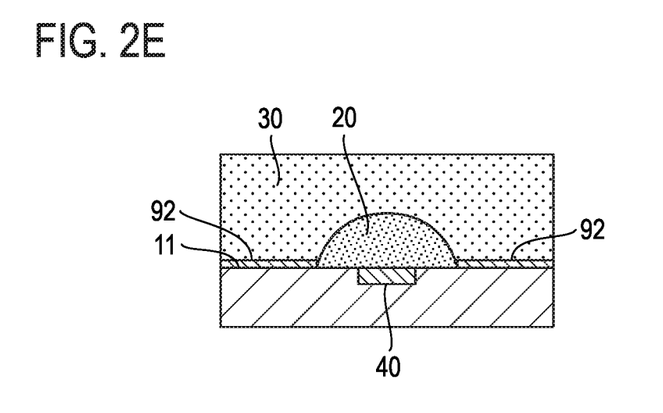
FIG. 2E is a diagram illustrating a fifth example of the structure that holds the first lump of liquid.

FIG. 2E shows example (d) in which no hydrophilization is performed and the region of the bottom surface 11 of the liquid bath 10 except the surface of the working electrode 40 and the annular portion is subjected to a hydrophobic treatment.

Figure 3A:
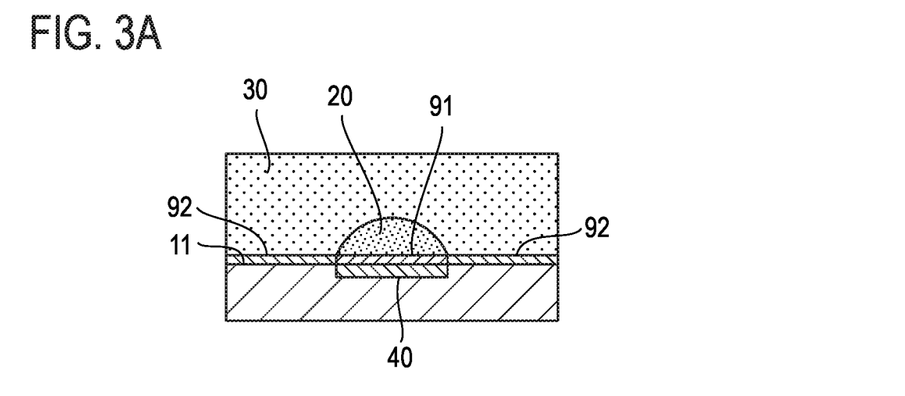
FIG. 3A is a diagram illustrating a sixth example of the structure that holds the first lump of liquid.

FIG. 3A shows example (e) in which the surface of the working electrode 40 is subjected to a hydrophilic treatment and the region of the bottom surface 11 of the liquid bath 10 other than the surface of the working electrode 40, that is, the region in contact with the second lump of liquid 30 is subjected to a hydrophobic treatment.

Figure 3B:
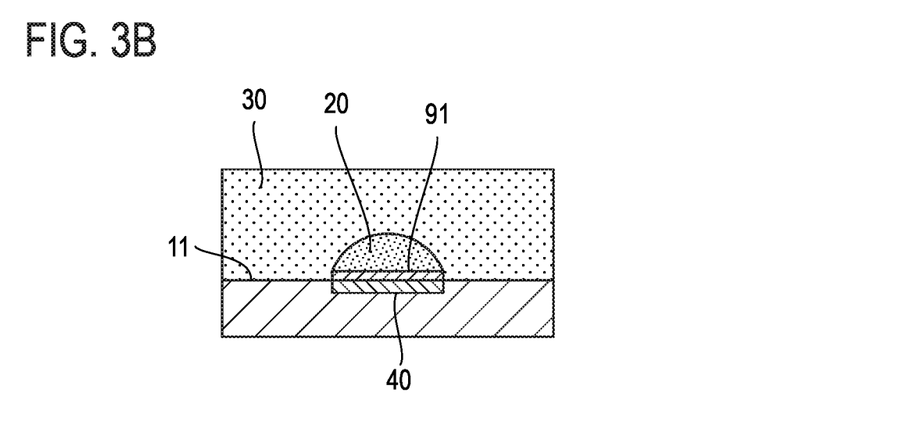
FIG. 3B is a diagram illustrating a seventh example of the structure that holds the first lump of liquid.

FIG. 3B shows example (a) in which the surface of the working electrode 40 is subjected to a hydrophilic treatment.

Figure 3C:
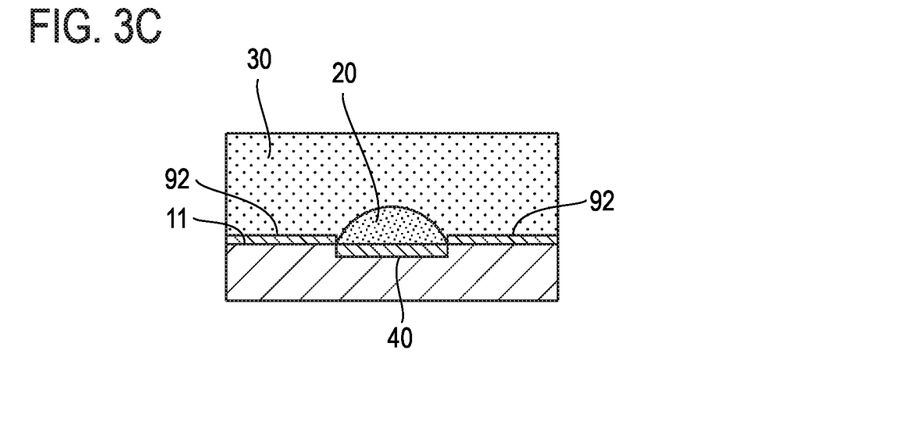
FIG. 3C is a diagram illustrating an eighth example of the structure that holds the first lump of liquid.

FIG. 3C shows example (d) in which no hydrophilization is performed and the region of the bottom surface 11 of the liquid bath 10 other than the surface of the working electrode 40, that is, the region in contact with the second lump of liquid 30 is subjected to a hydrophobic treatment.

Generally, the one first lump of liquid 20 on the bottom surface 11 of the liquid bath 10 is larger in size than the working electrode 40. Thus, the holding structures for the first lump of liquid 20 as shown in FIGS. 2A to 2E are adopted. However, the holding structures for the first lump of liquid 20 as shown in FIGS. 3A to 3C may also be adopted in light of the size of the working electrode 40 and the lump size of the first lump of liquid 20.

From the standpoint of strongly holding the first lump of liquid 20 to the surface of the working electrode 40, the structures in (e), (f) and (g) above as shown in FIG. 2A or FIG. 3A are preferable. However, it would be difficult to completely deny the possibility that detection sensitivity may degrade due to decrease of electron moving speed at the solid-liquid interface between the surface of working electrode 40 and the first lump of liquid 20, which is caused by hydrophilization of the working electrode 40. The holding structures for the first lump of liquid 20 shown in FIGS. 2B, 2D, 2E or FIG. 3C are preferable in light of avoidance of the sensitivity degradation.

Hydrophilization of the surface of the working electrode 40 can be performed by chemical treatment on the surface of the working electrode 40 using a hydrophilic agent having a hydrophilic group. When the material of the working electrode 40 is gold or platinum, examples of the hydrophilic agent include 2-mercaptoethanesulfonic acid, 2-amino-1-ethanethiol, and 3-mercaptopropionic acid. These hydrophilic agents have in a molecule a functional group that can be selectively combined with gold or platinum, and thus by only applying a solution containing these hydrophilic agents to the bottom surface 11 of the liquid bath 10, it is possible to selectively apply chemical treatment to only the surface of the working electrode 40.

When the hydrophilic agent is, for instance, 2-amino-1-ethanethiol or 3-mercaptopropionic acid, it is also possible to use the active amino group or the carboxyl group introduced onto the working electrode 40 as anchor molecules in the process of binding treatment of a capture antibody onto the working electrode 40, which will be performed later.

Next, hydrophilization of the annular portion which is part of the bottom surface 11 of the liquid bath 10 and surrounds the surface of the working electrode 40 will be described. The working electrode 40 is generally formed on, for instance, a substrate and this substrate is located on or at the bottom surface 11 of the liquid bath 10. Thus, the annular portion surrounding the surface of the working electrode 40 is, for example, part of a surface of a substrate.

When material of the substrate is, for instance, glass, quartz, aluminum oxide or silicon, or when a silicon nitride film is formed on the surface of the silicon, hydrophilization of the surface of the substrate can be achieved by surface treatment with, for instance, silane coupling agent including in a molecule a hydrophilic group such as a hydroxyl group, an amino group, a carboxyl group, which is performed after temporarily activating the surface through, for instance, ashing process or UV (ultraviolet) ozone process.

When a substrate in which the working electrode 40 is formed is located at the bottom surface 11 of the liquid bath 10, the second lump of liquid 30 is located on the substrate.

Hydrophobization of the surface of the substrate can be performed by photolithography using hydrophobic photosensitive resin. The method allows only a predetermined region to be selectively subjected to a hydrophobic treatment. Alternatively, only a portion that is not subjected to a hydrophobic treatment is masked with appropriate photosensitive resin, the whole substrate surface is treated with a hydrophobic agent, and then the photosensitive resin used for masking is dissolved and removed using a solvent, resulting in selective hydrophobization of the surface of the substrate. When material of the substrate is the aforementioned material, organic silane compound having a hydrophobic group such as di(trimethylsilyl)amine, chlorodimethyl(octadecyl)silane can be used as the hydrophobic agent.

Next, the holding structure for the first lump of liquid 20 using a well will be described with reference to FIG. 4.

Figure 4A:
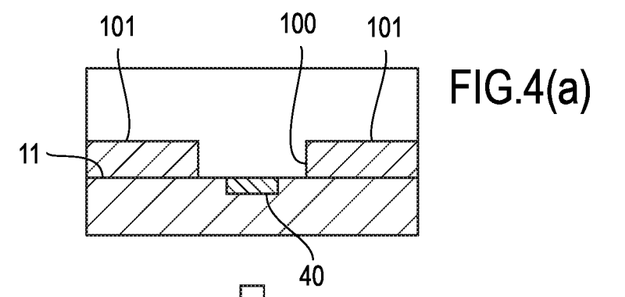
FIG. 4(a) is a schematic diagram of a well.

FIG. 4(1) shows the bottom surface 11 of the liquid bath 10 with a well 100 formed thereat. The working electrode 40 is located at the bottom of the well 100. The well 100 can be formed by photolithography using, for example, photosensitive resin. In the drawing, reference numeral 101 denotes a layer of hardened resin.

Figure 4B:
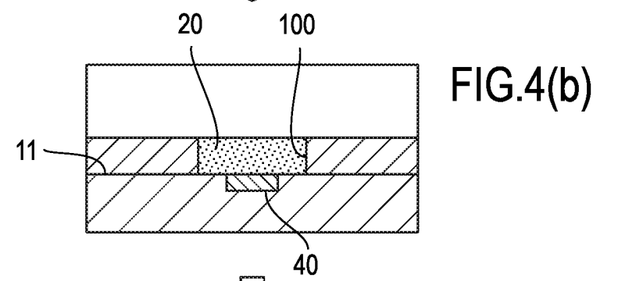
FIG. 4(b) is a schematic diagram illustrating a state in which the first lump of liquid is introduced into the well.
Figure 4C:
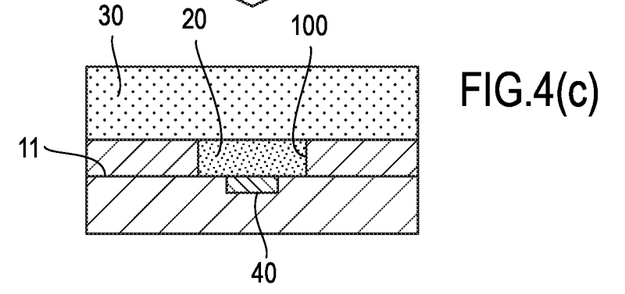
FIG. 4(c) is a schematic diagram illustrating a state in which the second lump of liquid covers the first lump of liquid.

FIG. 4(2) shows the well 100 with the first lump of liquid 20 introduced thereinto by dropping. FIG. 4(3) further shows the liquid bath 10 with the second lump of liquid 30 introduced thereinto. The aforementioned first lump of liquid 20 can be used as the herein-described first lump of liquid 20 and the aforementioned second lump of liquid 30 can be used as the herein-described second lump of liquid 30. The first lump of liquid 20 can be held onto the working electrode 40 by the well 100.

When two or more working electrodes 40 arranged in an array are located at the bottom surface 11 of the liquid bath 10, two or more wells 100 arranged in an array in a one-to-one correspondence with the two or more working electrodes 40 are formed at the bottom surface 11 of the liquid bath 10 and each of the working electrodes 40 is located at the bottom of a corresponding one of the wells 100. Each of the two or more wells 100 stores the first lump of liquid 20.

Figure 5:
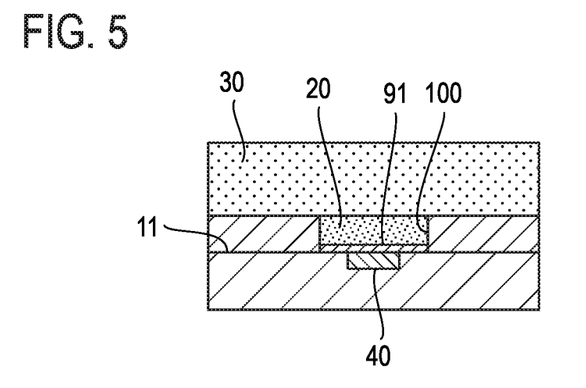
FIG. 5 is a diagram illustrating another example of the structure that holds the first lump of liquid.

FIG. 5 shows an example in which the same hydrophilization as the aforementioned hydrophilization is applied to the surface of the working electrode 40 and a portion of the bottom surface of the liquid bath 10 located in the area of the bottom of the well 100, or to be more specific, a portion of the surface of the substrate surrounding the surface of the working electrode 40 in order to more satisfactorily hold the first lump of liquid 20 in the well 100. In this way, the inner bottom surface of the well 100 may also be subjected to the herein-described hydrophilic treatment. Note that a hydrophilic-treated region 91 may be limited only to the surface of the working electrode 40 or only to the annular portion surrounding the surface of the working electrode 40 of the inner bottom surface of the well 100.

The electrochemical detection method of the present embodiment produces the following effects.

1) Because the first lump of liquid 20 is covered with the second lump of liquid 30, it is possible to prevent evaporation of the first lump of liquid 20. Thus, an object to be detected can be detected with high sensitivity.

2) Compared to a method requiring a relatively large-scale measuring apparatus and using quite an expensive substrate such as spectroscopic measurement, it is possible to inexpensively detect an object to be detected with a compact apparatus configuration.

3) When N is a predetermined integer equal to or greater than 2, in multi-point detection processing (that is, comprehensive multi-point detection processing) that performs N detection processes simultaneously using N working electrodes 40, crosstalk can be prevented because different first lumps of liquid 20 are separated by the second lump of liquid 30. Therefore, it is possible to detect an object to be detected with high sensitivity.

4) Although a small amount of the first lump of liquid 20 is used to improve the concentration of the catalytic reaction product, it is not necessary to use a micro counter electrode 50 and/or a micro reference electrode 60 because the counter electrode 50 and the reference electrode 60 are arranged in the second lump of liquid 30. Thus, it is possible to use the counter electrode 50 and the reference electrode 60 used in the prior art.

5) In multi-point detection, one counter electrode 50 and one reference electrode 60 may be prepared in the liquid bath 10 for the working electrodes 40. Therefore, it is possible to detect an object to be detected with a compact apparatus configuration with high sensitivity.

The electrochemical detection method of the present embodiment is applicable to a detection scheme in which: the product of a catalytic reaction progressing in the first lump of liquid 20 is the object to be detected; the concentration of the catalytic reaction product in the first lump of liquid 20 increases as the catalytic reaction progresses; the catalytic reaction product can be electrochemically detected; and the second lump of liquid 30 that dissolves the catalytic reaction product can be chosen.

ELISA uses an enzyme as a catalyst, but the catalyst is not limited to an enzyme. Examples of the catalyst may include metal catalyst, ribozyme, cells containing enzymes on the surface thereof or inside, organelle, minute particles that artificially adsorb or are artificially bound to these elements, and vesicle.

The sandwich ELISA forms a composite of capture antibody, antigen, primary antibody and enzyme-labeled secondary antibody, and thereby causes the catalyst to be indirectly bound to the solid phase, but the catalyst binding method is not limited to this. For example, the catalyst may be indirectly bound to the solid phase by hybridizing a probe DNA preliminarily bound to the solid phase surface with a single-strand DNA complementary with the probe DNA and labeled with the catalyst.

Alternatively, the catalyst may be indirectly bound to the solid phase by making antigen, peptide or sugar chain, these being preliminarily bound to the surface of the solid phase, interact with an antibody or a lectin that can specifically bind to those molecules and are labeled with the catalyst.

Such a binding method is already well known in expression analysis of using a DNA chip or a protein chip.

Alternatively, when measuring activity of the catalyst itself, the catalyst may be directly bound to the surface of the solid phase.

Figure 7:
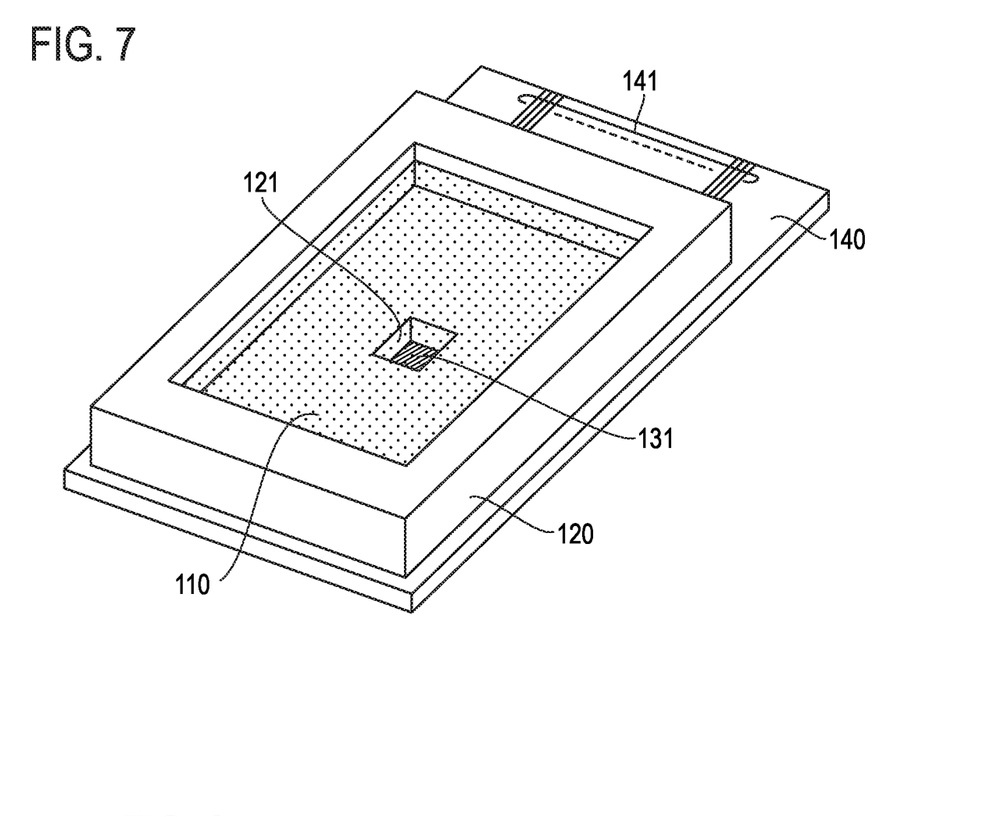
FIG. 7 is a perspective view of the transducer shown in FIG. 6A.
Figure 8:
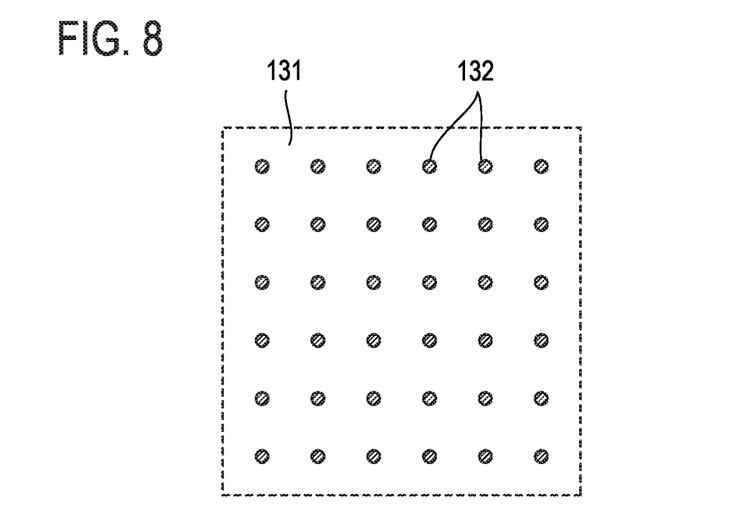
FIG. 8 is a diagram for describing an array of electrodes in the transducer shown in FIG. 6A.

Next, an embodiment of a transducer suitable for the aforementioned electrochemical detection of the catalytic reaction product will be described with reference to FIGS. 6 to 8.

The transducer of the present embodiment has a structure in which a liquid bath 120 that can contain a solution 110 is mounted on an LSI chip (large scale integrated chip) 130. The liquid bath 120 has hole 121 at the center thereof and the LSI chip 130 is placed at lower end of the hole 121 and covers the hole 121.

The LSI chip 130 and the liquid bath 120 are fixed to a substrate 140 and a wiring pattern 141 for connecting the LSI chip 130 to an external apparatus that controls the transducer is formed on the substrate 140. Reference numeral 150 in FIG. 6B denotes a bonding wire for connecting the LSI chip 130 to the wiring pattern 141.

A sensor region 131 is formed on the top surface of the LSI chip 130. The sensor region 131 is located in the hole 121 at the bottom surface of the liquid bath 120.

Although details are omitted in FIGS. 6A, 6B and 7, 400 electrodes 132 of φ40 μm that function as working electrodes are formed in the sensor region 131 in this example. The 400 electrodes 132 constitute a 20×20 array, and are arranged at intervals of 250 μm. FIG. 8 shows part of the sensor region 131 in which the electrodes 132 are formed. The material of the electrodes 132 is gold in this example and a silicon nitride film is formed on the top surface of the LSI chip 130 including at least the sensor region 131 except the electrodes 132. The LSI chip 130 has a function to detect currents generated by oxidation reduction reaction between each electrode 132 and an object to be detected, and amplify the respective detected currents.

In the LSI chip 130, the above-described holding structures (see FIGS. 2A, 2B, 2C, 2D, 2E, 3A, 3B, 3C, 4 and 5) are applied to each electrode 132 and the sensor region 131. For example, the hydrophilization shown in FIG. 2 and FIG. 3 is applied to the surface of each electrode 132 and an annular surface surrounding the surface of each electrode 132, or the well shown in FIG. 4 and FIG. 5 is formed. The transducer of the embodiment can strongly hold the first lumps of liquid in which a catalytic reaction progresses to the electrodes 132 by using the holding structures. In FIGS. 6A, 6B and 7, the solution 110 is the second lump of liquid that covers the first lumps of liquid, and the first lumps of liquid are not shown.

Figure 6A:
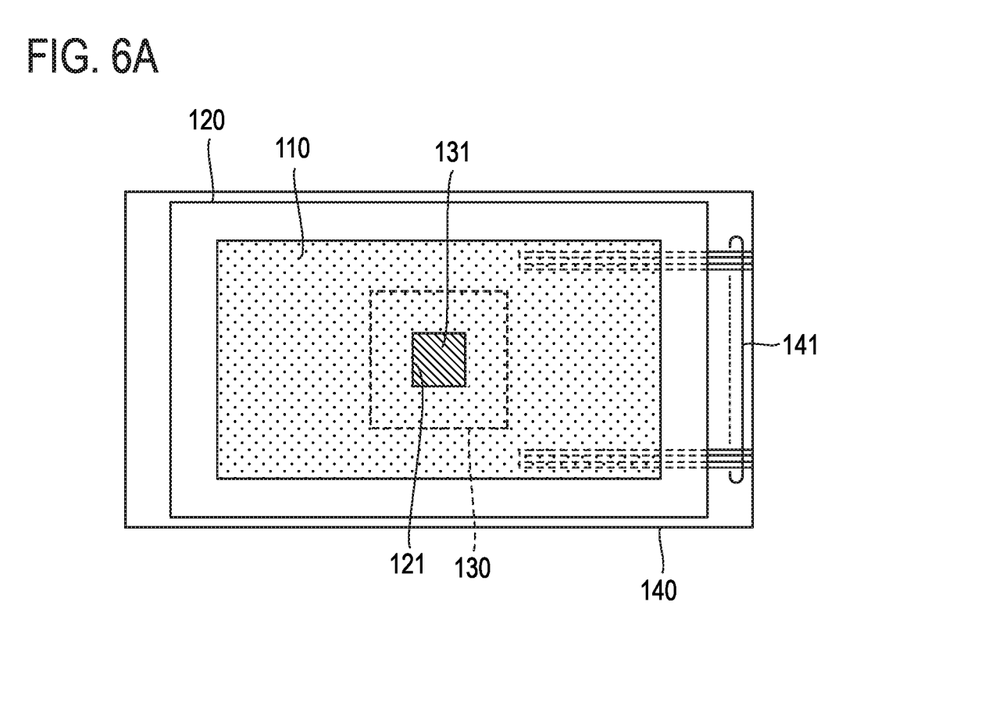
FIG. 6A is a plan view illustrating an embodiment of a transducer.
Figure 6B:
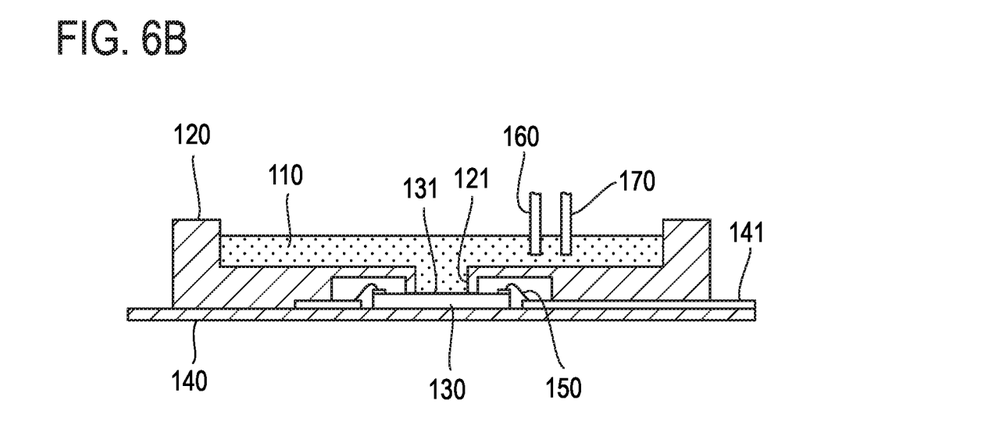
FIG. 6B is a cross-sectional view illustrating the embodiment of the transducer.

A counter electrode 160 and a reference electrode 170 shown in FIGS. 6A and 6B are not necessarily essential components of the transducer.

The counter electrode 160 and the reference electrode 170 are introduced into the second lump of liquid before implementing the method of the present embodiment.

<Addendum>

Although the present invention has been described with reference to the illustrative embodiment, those skilled in the art will understand that various changes can be made without departing from the scope of the present invention and the elements thereof can be replaced by equivalents. Moreover, many modifications can be made to adapt a specific system, device or components thereof to the teachings of the present invention without departing from the intrinsic scope of the present invention. Therefore, the present invention is not limited to a specific embodiment disclosed to implement the present invention, but includes all embodiments included in the appended scope of claims.

Furthermore, the terms like "first," "second" or the like are used not to indicate order or importance, but to distinguish the elements. The terms used in the present specification is intended to describe the embodiment and is in no way intended to limit the present invention. The term "include" and inflections thereof, when used in the present specification and/or the appended scope of claims, clarify the presence of the mentioned features, steps, operations, elements and/or components, but do not exclude the presence or addition of one or a plurality of other features, steps, operations, elements, components and/or the group thereof. The term "and/or" includes, if present, one or a plurality of all sorts of combinations of related and listed elements. In the scope of claims and the specification, "connection," "combination," "joining," "coupling" or synonyms thereof and all inflections thereof do not necessarily deny the presence of one or more "interconnected" or "combined" or "coupled" intermediate elements unless otherwise specified.

All terms used in the present specification (including technical terms and scientific terms) have the same meanings generally understood by those skilled in the art to which the present invention belongs unless otherwise specified. Furthermore, terms such as those defined in commonly used dictionaries should be interpreted as having meanings consistent with meanings in context of the related arts and the present disclosure, and should not be interpreted ideally or excessively formally unless explicitly defined.

It will be understood that the present invention has disclosed many techniques and steps in the description thereof. Those techniques and steps have their respective individual advantages and can also be used in combination with one or more or, in some cases, all of other disclosed techniques. Therefore, to avoid complications, the present specification refrains from describing all possible combinations of the individual techniques or steps. However, the specification and claims should be read with an understanding that such combinations are totally included in the present invention and the scope of claims.

In the following claims, corresponding structures, materials, actions and equivalents of all functional elements combined with parts or steps, if present, are intended to include structures, materials or actions to execute functions in combination with other claimed elements.

Although the embodiment of the present invention has been described so far, the present invention is not limited to the embodiment. Various changes and modifications are allowed without departing from the spirit of the present invention. The selected and described embodiment is intended to describe principles of the present invention and practical applications thereof. The present invention is used as various embodiments along with various changes or modifications, and the various changes or modifications are determined according to expected use. All such changes and modifications are intended to be included in the scope of the present invention defined by the appended claims, and are intended to be granted the same protection when interpreted according to a range given impartially, legally and fairly.

DESCRIPTION OF REFERENCE NUMERALS 10 liquid bath
11 bottom surface
20 first lump of liquid
30 second lump of liquid
40 working electrode
50 counter electrode
60 reference electrode
70 salt bridge
80 potentiostat
81 variable power supply
82 voltmeter
83 ammeter
91 hydrophilic-treated region
92 hydrophobic-treated region
100 well
101 resin layer
110 solution
120 liquid bath
121 hole
130 LSI chip
131 sensor region
132 electrode
140 substrate
141 wiring pattern
150 bonding wire
160 counter electrode
170 reference electrode

What is claimed is:

1. A method of electrochemically detecting a catalytic reaction product generated and dissolved in a first lump of liquid, the catalytic reaction product being generated by a catalytic reaction progressing in the first lump of liquid, the method comprising:
   a step a) of containing the first lump of liquid and a second lump of liquid in a liquid bath, the second lump of liquid being in contact with the first lump of liquid to form a liquid-liquid interface and, wherein the catalytic reaction product is insoluble in the second lump of liquid;
   a step b) of arranging a working electrode in the first lump of liquid and arranging a counter electrode and a reference electrode in the second lump of liquid; and
   a step c) of detecting a current flowing through the working electrode caused by an oxidation or reduction reaction of the catalytic reaction product, the oxidation or reduction reaction occurring at the working electrode.

2. The method according to claim 1, wherein
the step a) further comprises containing one or more other first lumps of liquid, the second lump of liquid being in contact with the one or more other first lumps of liquid to form liquid-liquid interfaces, respectively, such that the one or more other first lumps of liquid are separated from each other by the second lump of liquid,
the step b) further comprises arranging one or more other working electrodes in the one or more other first lumps of liquid, respectively, such that each of the one or more other working electrodes is covered with a corresponding one of the one or more other first lumps of liquid, and
the step c) further comprises detecting one or more other currents flowing through the one or more other working electrodes, respectively, caused by one or more other oxidation or reduction reactions of one or more other catalytic reaction products, respectively, the one or more other catalytic reaction products being generated and dissolved in the one or more other first lumps of liquid, respectively, but insoluble in the second lump of liquid, the one or more other catalytic reaction products being generated by one or more other catalytic reactions progressing in the one or more other first lumps of liquid, respectively, and the one or more other oxidation or reduction reactions occurring at the one or more other working electrodes, respectively, whereby the one or more other catalytic reaction products may be electrochemically detected together with the catalytic reaction product.

3. The method according to claim 1, wherein
the working electrode is located at a bottom surface of the liquid bath, and
the first lump of liquid is located on the bottom surface and covered with the second lump of liquid.

4. The method according to claim 2, wherein
the working electrode and the one or more other working electrodes are located at a bottom surface of the liquid bath, and
the first lump of liquid and the one or more other first lumps of liquid are located on the bottom surface and covered with the second lump of liquid.

5. The method according to claim 3, wherein at least one of a surface of the working electrode and an annular portion of the bottom surface which surrounds the surface of the working electrode has a hydrophilicity.

6. The method according to claim 4, wherein surfaces of the working electrode and the one or more other working electrodes and/or annular portions of the bottom surface which surround surfaces of the working electrode and the one or more other working electrodes, respectively, have a hydrophilicity.

7. The method according to claim 3, wherein a region of the bottom surface where the second lump of liquid is located has a hydrophobicity.

8. The method according to claim 4, wherein a region of the bottom surface where the second lump of liquid is located has a hydrophobicity.

9. The method according to claim 5, wherein a region of the bottom surface where the second lump of liquid is located has a hydrophobicity.

10. The method according to claim 6, wherein a region of the bottom surface where the second lump of liquid is located has a hydrophobicity.

11. The method according to claim 1, wherein
a well is configured on a bottom surface of the liquid bath, and
the working electrode and the first lump of liquid are located in the well.

12. The method according to claim 2, wherein
two or more wells are configured on a bottom surface of the liquid bath, the two or more wells being in a one-to-one correspondence with the working electrode and the one or more other working electrodes,
each of the working electrode and the one or more other working electrodes is located in a corresponding one of the two or more wells, and
each of the first lump of liquid and the one or more other first lumps of liquid is located in a corresponding one of the two or more wells.

13. The method according to claim 11, wherein
at least one of a surface of the working electrode and an annular portion of an inner bottom surface of the well which surrounds the surface of the working electrode has a hydrophilicity.

14. The method according to claim 12, wherein
surfaces of the working electrode and the one or more other working electrodes and/or annular portions of inner bottom surfaces of the two or more wells which surround the surfaces of the working electrode and the one or more other working electrodes, respectively, have a hydrophilicity.

15. A transducer for electrochemically detecting a catalytic reaction product generated by progress of a catalytic reaction in a solution, the transducer comprising:
an LSI chip;
a liquid bath for containing the solution mounted on the LSI chip, the liquid bath having a bottom surface on which a sensor region is defined; and
electrodes arranged in an array provided on the LSI chip, the electrodes being located in the sensor region, the electrodes having surfaces associated therewith such that the bottom surface of the liquid bath have annular portions which surround the surfaces of the electrodes, respectively, wherein
the transducer is characterized in that at least one of a combination of the surfaces of the electrodes and a combination of the annular portions of the bottom surface has a hydrophilicity and/or the transducer is characterized in that the sensor region except the surfaces of the electrodes and the annular portions of the bottom surface has a hydrophobicity.

16. A transducer for electrochemically detecting a catalytic reaction product generated by progress of a catalytic reaction in a solution, the transducer comprising:
an LSI chip;
a liquid bath for containing the solution mounted on an LSI chip, the liquid bath having a bottom surface on which a sensor region is defined, wherein wells arranged in an array are formed in the sensor region, each of the wells having an inner bottom surface associated therewith; and
electrodes having surfaces associated therewith provided on the LSI chip, each of the electrodes being located in a corresponding one of the wells such that each of the surfaces of the electrodes is surrounded by an annular portion of the inner bottom surface of the corresponding one of the wells, wherein
the surfaces of the electrodes and/or the annular portions of the inner bottom surfaces have a hydrophilicity.

* * * * *